(12) United States Patent
Kojima

(10) Patent No.: US 6,672,136 B2
(45) Date of Patent: Jan. 6, 2004

(54) GAS SENSOR HAVING IMPROVED STRUCTURE OF ELECTRIC CONNECTOR

(75) Inventor: Takashi Kojima, Kasugai (JP)

(73) Assignee: Denso Corporation, Kariya (JP)

( * ) Notice: Subject to any disclaimer, the term of this patent is extended or adjusted under 35 U.S.C. 154(b) by 119 days.

(21) Appl. No.: 09/820,754

(22) Filed: Mar. 30, 2001

(65) Prior Publication Data

US 2001/0025522 A1 Oct. 4, 2001

(30) Foreign Application Priority Data

Mar. 30, 2000 (JP) .......................................... 2000-95156
Feb. 9, 2001 (JP) .......................................... 2001-34178

(51) Int. Cl.⁷ ............................. G02N 7/00; G02N 27/26
(52) U.S. Cl. ....................... 73/31.05; 73/23.31; 204/424
(58) Field of Search ............................. 73/23.31, 31.05, 73/23.32, 31.06; 204/424–429

(56) References Cited

U.S. PATENT DOCUMENTS

| | | | | |
|---|---|---|---|---|
| 4,556,475 A | * | 12/1985 | Bayha et al. ............... | 174/75 R |
| 4,983,271 A | * | 1/1991 | Kato et al. .................. | 204/426 |
| 5,246,562 A | * | 9/1993 | Weyl et al. ................. | 204/424 |
| 5,490,412 A | * | 2/1996 | Duce et al. ................. | 73/118.1 |
| 5,546,787 A | * | 8/1996 | Hafele et al. ............... | 204/426 |
| 5,602,325 A | * | 2/1997 | McClanahan et al. ...... | 204/424 |
| 5,711,863 A | * | 1/1998 | Henkelmann et al. ...... | 204/424 |
| 5,922,938 A | * | 7/1999 | Hafele ........................ | 204/426 |
| 6,082,175 A | | 7/2000 | Yoshikawa et al. | |
| 6,311,543 B1 | * | 11/2001 | Yoshikawa et al. ......... | 73/23.2 |

FOREIGN PATENT DOCUMENTS

| | | |
|---|---|---|
| JP | 61-70763 | 5/1986 |
| JP | 8-1493 | 1/1996 |
| JP | 10-253579 | 9/1998 |
| WO | WO 92/08127 | 5/1992 |

* cited by examiner

*Primary Examiner*—Michael Cygan
(74) *Attorney, Agent, or Firm*—Nixon & Vanderhye, PC

(57) ABSTRACT

An improved structure of a gas sensor is provided which is designed to establish firm electric connections between electrode terminals formed on opposed major surfaces of a sensor element and terminals of a connector disposed within a body of the gas sensor leading to an external devices. The connector includes two arrays of terminals. Each of the terminals has a contact elastically deformable at least in a direction perpendicular to the opposed major surfaces of the sensor element for keeping the electric connections of the electrode terminals and the terminals of the connector constant.

10 Claims, 11 Drawing Sheets

GAS SENSOR HAVING IMPROVED STRUCTURE OF ELECTRIC CONNECTOR

BACKGROUND OF THE INVENTION

1. Technical Field of the Invention

The present invention relates generally to a composite gas sensor which may be employed in an air-fuel ratio control system measuring the concentrations of different components contained in exhaust gasses of an internal combustion engine of automotive vehicles, and more particularly to an improvement on an electric connector used in such a composite gas sensor.

2. Background Art

Gas sensors equipped with a sensor element made up of a laminated plate are known for use in burning control of fuel in internal combustion engines of modern automotive vehicles. Gas sensors of this type generally have disposed therein a connector electrically coupled through leads to electrodes provided on the sensor element for use in picking up a sensor output and supplying the power to a heater provided on the sensor element. The leads extend outside the gas sensor and connect with an external device.

In recent years, there is an increasing need for composite sensor elements. The composite sensor elements are each designed to measure concentrations of different gas components simultaneously. For instance, in a case of automotive vehicles, the composite sensor element is used to measure NOx and $O_2$ contents and an air-fuel ratio of exhaust gasses simultaneously. For precise measurement, composite sensor elements equipped with a plurality of electrochemical cells are being used. Sensor elements of this type must have many electrodes for the cells.

However, if a sensor element of the above type is installed in a gas sensor equipped with a connector such as one taught in Japanese Utility Model Second Publication No. 8-1493, a drawback is encountered in that it is difficult to establish firm engagement of the connector with electrodes of the sensor element, which may result in electric disconnections of the connector and the electrodes.

The gas sensor as taught in the above publication includes electrode terminals provided on an end of the sensor element remote from a sensing portion, a metallic sensor element holder, a receptacle leading to the electrode terminals, a ceramic housing having disposed therein the receptacle in isolation from the holder, a spring, and a staking ring pressing a spring to produce a spring pressure for holding leads. The staking ring has extensions formed around the periphery thereof which make a connection of the staking ring and an end portion of the holder. Therefore, there are drawbacks in that the use of the staking ring increases production costs and results in complexity of assembly of the gas sensor.

Japanese Utility Model First Publication No. 61-70763 discloses a gas sensor which includes an insulation porcelain, four spring plates disposed in the insulation porcelain, and a sensor element having electrode terminals. The sensor element is mounted in the insulation porcelain in electric contact with the spring plates. The sensor element has two of the electrode terminals provided on one surface thereof because it is difficult to provide three or more electrode terminals on one surface for a narrow internal space of the insulation porcelain.

SUMMARY OF THE INVENTION

It is therefore a principal object of the invention to avoid the disadvantages of the prior art.

It is another object of the invention to provide an improved structure of a gas sensor constructed to make firm electric connections between electrode terminals of a sensor element and a connector and to be assembled easily.

According to one aspect of the invention, there is provided a gas sensor which comprises: (a) a hollow cylindrical housing; (b) a sensor element made of a laminated plate which includes sensing portion and a base portion opposite the sensing portion and which has an array of electrode terminals formed on each of opposed surfaces of the base portion, the sensor element being retained at an sensing portion thereof by an insulation porcelain within the housing; (c) a cover covering the base portion of the sensor element; and (d) a connector disposed within the cover, the connector having arrays of terminals which each array is connected electrically to one of the arrays of electrode terminals of the sensor element, each of the terminals including a contact which is elastically deformable at least in a direction substantially perpendicular to the opposed surfaces of the sensor element to establish a firm electric connection to one of the electrode terminals of the sensor element.

In the preferred mode of the invention, the connector also includes insulating members. A retaining spring member is further disposed within the cover to elastically retain each of the arrays of terminals of the connector through one of the insulating members so as to urge the terminals of the connector into constant contact with the electrode terminals of the sensor element.

The insulating members are made of one of a ceramic material and a resin material.

The connector may have two terminal arrays each made up of four terminals making the electric connections to the electrode terminals of the sensor element, respectively.

An elastic pressure produced by the retaining spring member to urge the terminals of the connector into constant contact with the electrode terminals of the sensor element is set greater than or equal to a total of elastic pressures produced by elastic deformation of the contacts of the terminals of the connector in the direction perpendicular to the opposed surfaces of the sensor element.

The elastic pressure produced by the elastic deformation of the contacts of the terminals of the connector is so set as to absorb a gap between each of the contacts and a corresponding one of the electrode terminals of the sensor element.

Each of the insulating members has an inner wall opposed to one of the surfaces of the sensor element, an end wall facing a tip of the sensing portion of the sensor element, and an outer wall opposite the inner wall. Each of the terminals of the connector is curved in the shape of C so as to surround the inner wall, the end wall, and the outer wall of one of the insulating members.

Each of the terminals of the connector is made of one of a round conductive line and a rectangular conductive line.

Each of the terminals of the connector may have a hook fitted on an end of one of the insulating members so that half of the terminals are arrayed on the surface of one of the insulating members.

A second hollow insulation porcelain is further disposed within the cover. The retaining spring member includes a holding portion and a retaining portion. The holding portion holds the terminals of the connector through the insulating members. The retaining portion is placed in elastic engagement with an inner wall of the second hollow insulation porcelain so as to urge the terminals of the connector into constant contact with the electrode terminals of the sensor element.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

DESCRIPTION OF THE PREFERRED EMBODIMENTS

Figure 1:
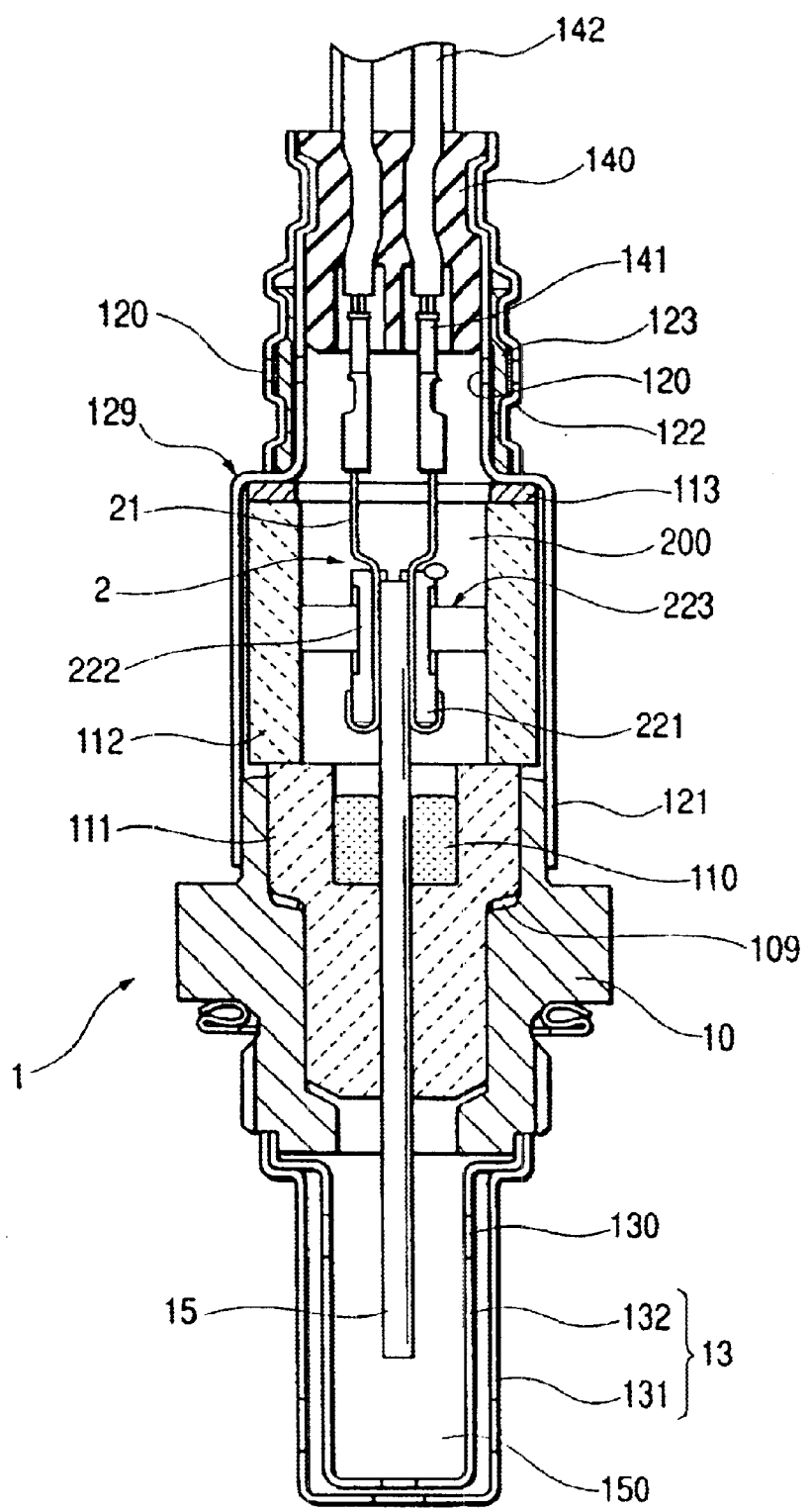
FIG. 1 is a longitudinal sectional view of a gas sensor according to the first embodiment of the invention.

Referring to the drawings, wherein like reference numbers refer to like parts in several views, particularly to FIG. 1, there is shown a gas sensor 1 according to the first embodiment of the invention which may be employed in a burning control system for automotive vehicles to measure concentrations of components such as NOx, CO, HC, $O_2$ contained in exhaust gasses of the engine.

The gas sensor 1 generally includes a sensor element 15, a laminated plate, a first insulation porcelain 111, a second insulation porcelain 112, a hollow cylindrical housing 10, and an outer cover 121. The sensor element 15 is made of a laminated plate. For example, U.S. Pat. No. 5,573,650, issued on Nov. 12, 1996 to Fukaya et al. teaches a typical laminated sensor element, disclosure of which is incorporated herein by reference. The first insulation porcelain 111 is fitted within the housing 10. The second insulation porcelain 112 is mounted on the first insulation porcelain in alignment with each other. The outer cover 121 is installed at an end thereof on the housing 10 to cover a base portion of the sensor element 15.

The second insulation porcelain 112 is made of a hollow cylindrical insulating member and has disposed therein a connector 2. The connector 2 is constructed to establish electric connections with four electrode terminals 151, as clearly shown in FIG. 3, formed on each of opposed major surfaces of the sensor element 15. Specifically, the connector 2 makes eight electric connections one with each of eight electrodes of the sensor element 15.

Figure 2A:
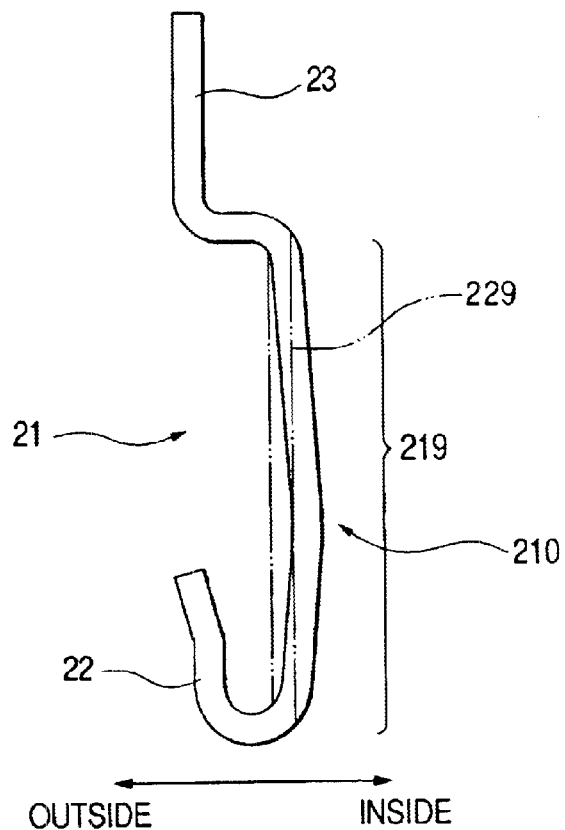
FIG. 2(a) shows each terminal pin arrayed in a connector.
Figure 5:
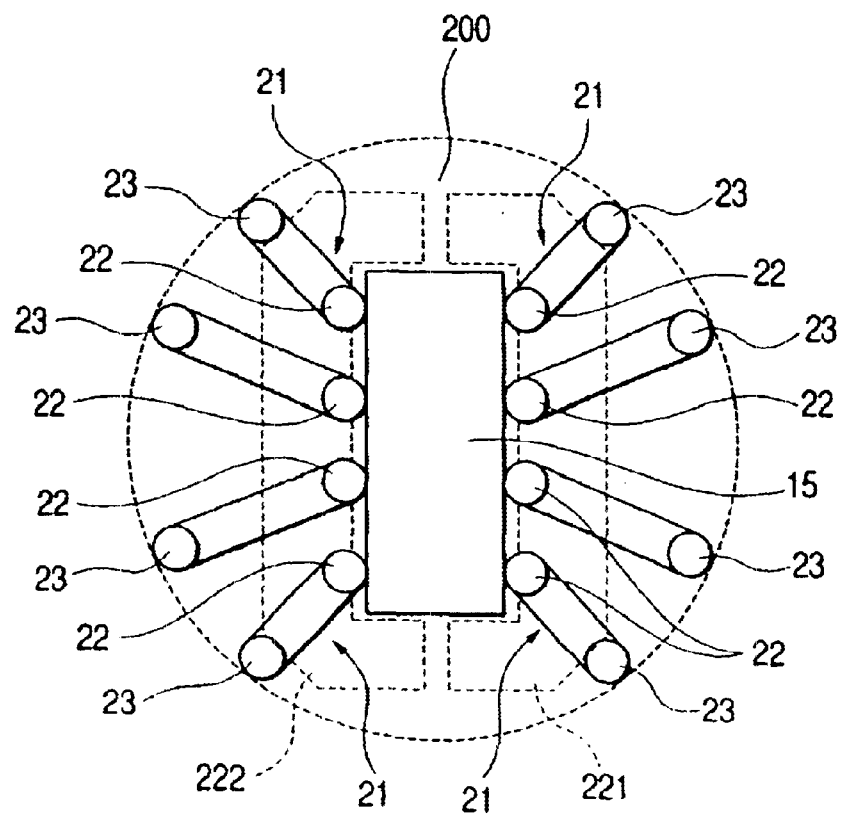
FIG. 5 is a top plan view which shows the connector of FIG. 4.
Figure 4:
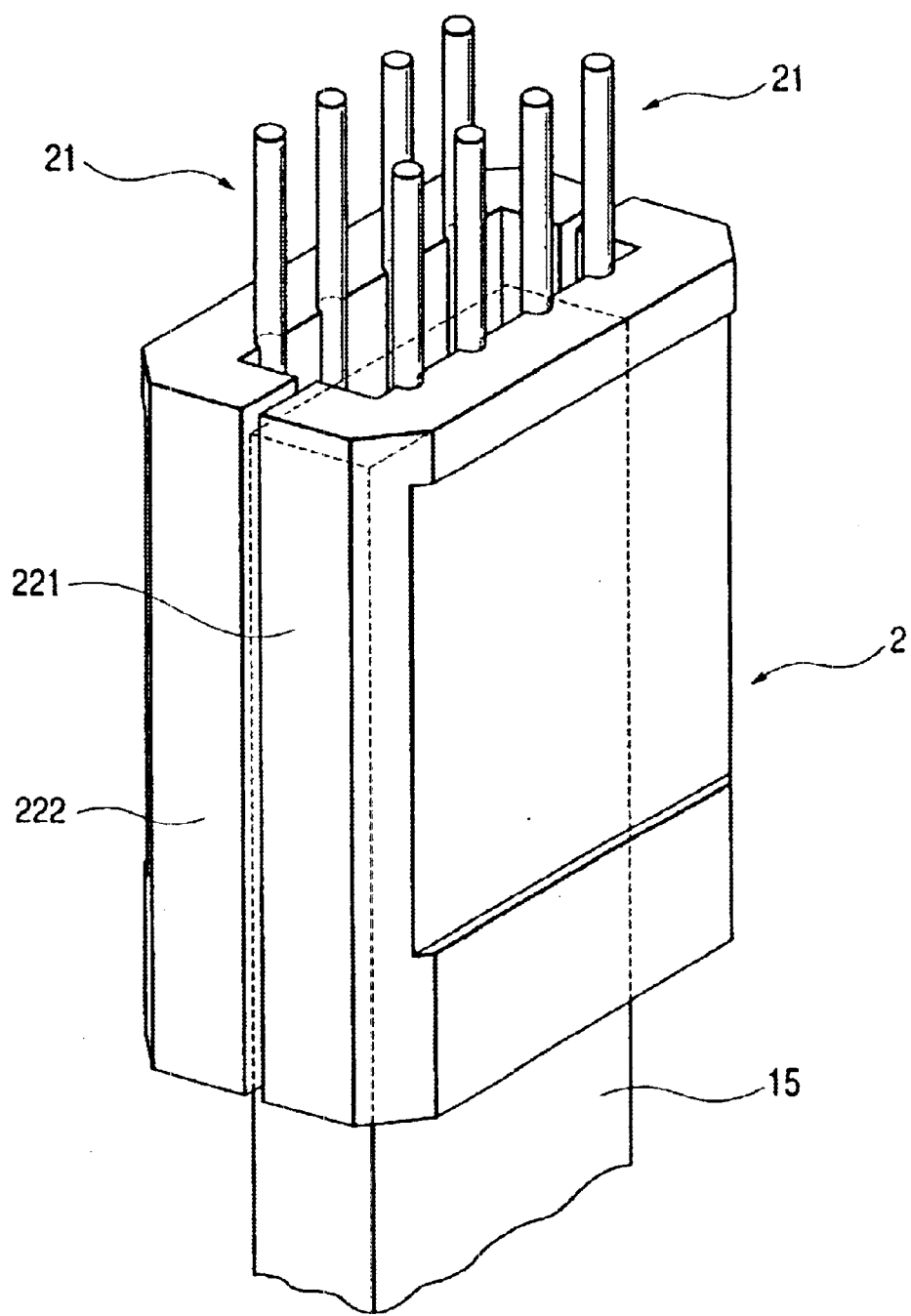
FIG. 4 is a perspective view which shows a connector of the first embodiment of the invention.

The connector 2, as shown in FIGS. 4 and 5, includes eight terminal pins 21 disposed therein which are made of a round wire, for example. Each of the terminal pins 21, as shown in FIG. 2(a), has an elastic contact 210 which is elastically deformable at least in a radius direction of the connector 2, that is, a lateral direction perpendicular to the major surfaces of the sensor element 15 for establishing a firm electric connection with one of the electrode terminals 151 of the sensor element 15. Each of the terminal pins 21 may alternatively be made of a conductor line having a rectangular in cross section.

The gas sensor 1 also includes, as shown in FIG. 1, a protective cover assembly 13 consisting of an outer cover 131 and an inner cover 132. The protective cover assembly 13 is installed on a head of the housing 10 to define a gas chamber 150 into which a gas to be measured is admitted through gas holes 130 formed in the outer and inner covers 131 and 132.

The first insulation porcelain 111 is retained within the housing 10 through a metallic packing ring 109 and holds therein the sensor element 15 through a glass sealing member 110. The second insulation porcelain 112 is, as described above, mounted on the first insulation porcelain 111 and surrounded by the outer cover 121. The outer cover 121 has an upper small-diameter portion, as viewed in the drawing, to form a shoulder 129. A disc spring 113 is disposed between the shoulder 129 and an end of the second insulation porcelain 112 to elastically urge the second insulation porcelain 112 into constant engagement with the first insulation porcelain 111.

A second metallic cover 122 is installed on the periphery of the small-diameter portion of the outer cover 121. The second metallic cover 122 is crimped to retain a water-repellent filter 123 around the small-diameter portion of the outer cover 121. The small-diameter portion of the outer cover 121 and the second metallic cover 122 have formed therein air vents 120 in alignment with each other for admitting air used as a reference gas in measuring the gas within the gas chamber 150.

An insulating holder 140 made of rubber is disposed inside the small-diameter portion of the outer cover 121 which has formed therein through holes into which leads 142 are inserted. The leads 142 are coupled to the terminal pins 21 of the connector 2, respectively, for picking up sensor outputs and supplying the power to the sensor element 15 from an external power source.

The second insulation porcelain 112 has an inner chamber 200 within which the connector 2 is retained by a retaining spring plate 223.

Each of the terminal pins 21 of the connector 2 is, as shown in FIG. 2(a), made of a round metallic wire which has a body portion 219 and an end portion curved outward to form a joint portion 23. The body portion 219 has formed on the center thereof the elastic contact 210. The terminal pins 21 are, as shown in FIG. 5, fitted within the inner chamber 200 of the second insulation porcelain 112 and coupled to the leads 142 through metallic joints 141. The body portion 219 is bent inwardly of the connector 2 (i.e., the gas sensor 1) to be deformable, as indicated by broken lines in FIG. 2(a), elastically in the radius direction of the connector 2 for securing an electric connection with the electrode terminal 151 through the elastic contact 219. The body portion 229 has an end folded upwardly, as viewed in the drawing, to form a hook 22. The connector 2 also includes a pair of insulating spacers 221 and 222, as shown in FIGS. 1 and 4, which work to insulate the terminal pins 21 from the retaining spring plate 223 and are retained in the second insulation porcelain 112 by the retaining spring plate 223. Each of the insulating spacers 221 and 222 is made of a ceramic material such as alumina ceramics or resin such as fluorine-contained polymers or polyamide-imide resin. Each of the hooks 22 of the terminal pins 21 is fitted on an end of one of the insulating spacers 221 and 222 to retain the body portion 219 on an inner wall of the one of the insulating spacers 221 and 222.

Figure 7:
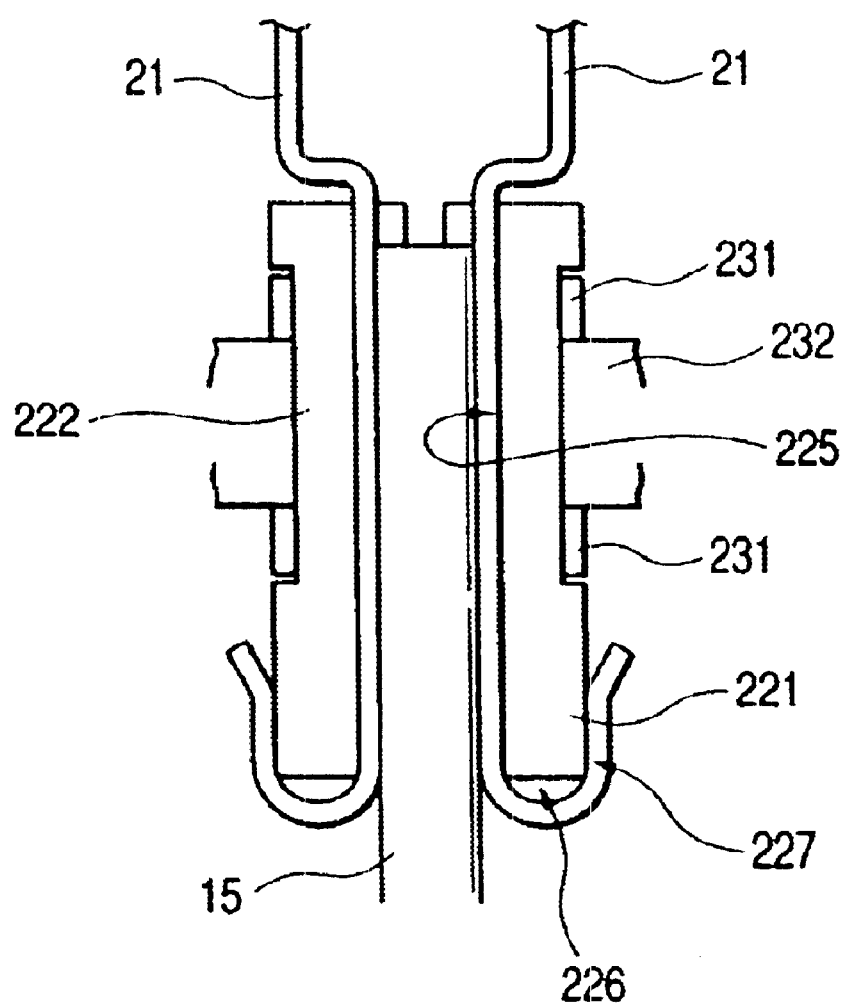
FIG. 7 is a partial view which shows terminals of a connector fitted on insulating spacers.

Each of the insulating spacers 221 and 222, as shown in FIG. 7, has an inner wall 225 extending in the longitudinal direction of the gas sensor 1, a head surface 226 oriented to the tip (i.e., a gas-sensing portion) of the gas sensor 1, and an outer surface 227 extending in parallel to the inner surface 225. Each of the terminal pins 21 extends in the form of a C-shape over the inner surface 225, the head surface 226, and the outer surface 227 of one of the insulating spacers 221 and 222 in engagement therewith.

Figure 6A:
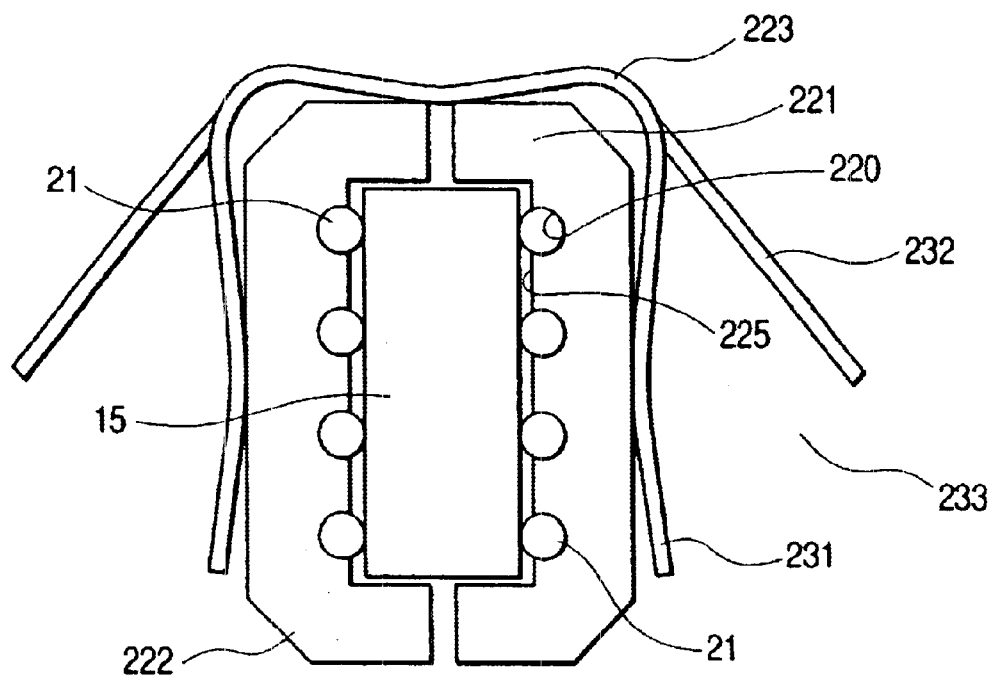
FIG. 6(a) is a top plan view which shows a retaining spring member which retains the connector of FIG. 4.

The insulating spacers 221 and 222, as shown in FIG. 6(a), holds therebetween the sensor element 15 so that they may be separated through a given air gap. Each of the insulating spacers 221 and 222 has formed in the inner wall 225 grooves 220 each of which retains one of the terminal pins 21. The insulating spacers 221 and 222 are, as described above, retained by the retaining spring plate 223 within the second insulation porcelain 112. The retaining spring plate 223, as clearly shown in FIG. 6(a), U-shaped holding portions 231 and a C-shaped spring portion 232. The holding portions 231 extend, as viewed in FIG. 7, on upper and lower sides of the spring portion 232 and hold therein the insulating spacers 221 and 222 elastically. The spring portion 232, as shown in FIGS. 6 and 7, extend outwardly between the holding portions 231 and abut at ends thereof against the inner wall of the second insulation porcelain 112 so as to produce spring loads urging the insulating spacers 221 and 222 inwardly, thereby pressing the terminal pins 21 against the surface of the sensor element 15 to keep firm electric connections with the electrode terminals 151, as shown in FIG. 3, formed on the opposed major surfaces of the sensor element 15.

Figure 6B:
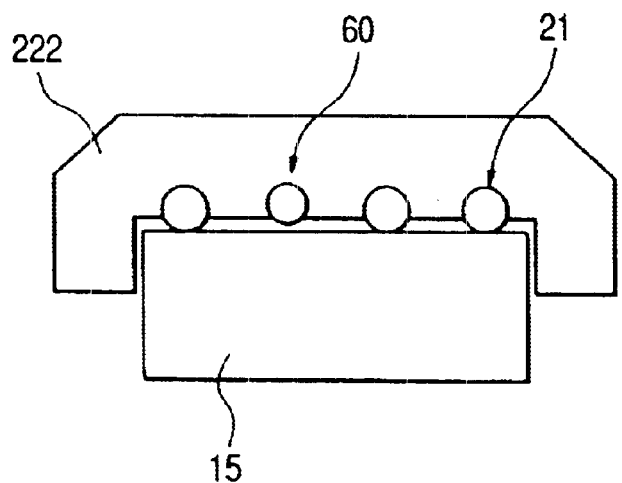
FIG. 6(b) shows a case in which there is an air gap between one of terminals and an electrode terminal of a sensor element.

Therefore, even if any one of the terminal pins 21 is, as indicated at 60 in FIG. 6(b), smaller in diameter than the other terminal pins 21 or has the body portion 219 (i.e., the elastic contact 210) different in shape from those of the other terminal pins 21, it is placed in electric contact with one of the electrode terminals 151 on the sensor element 15 by the spring loads exerted inwardly by the spring portions 232 of the retaining spring plate 223.

It is advisable that the spring load exerted by the spring portion 232 of the retaining spring plate 223 on one of the insulating spacers 221 and 222 be set more than or equal to the total of elastic pressures to be produced by the four terminals pins 21 for securing the electric connections between the terminal pins 21 and the electrode terminals 151.

Figure 2B:
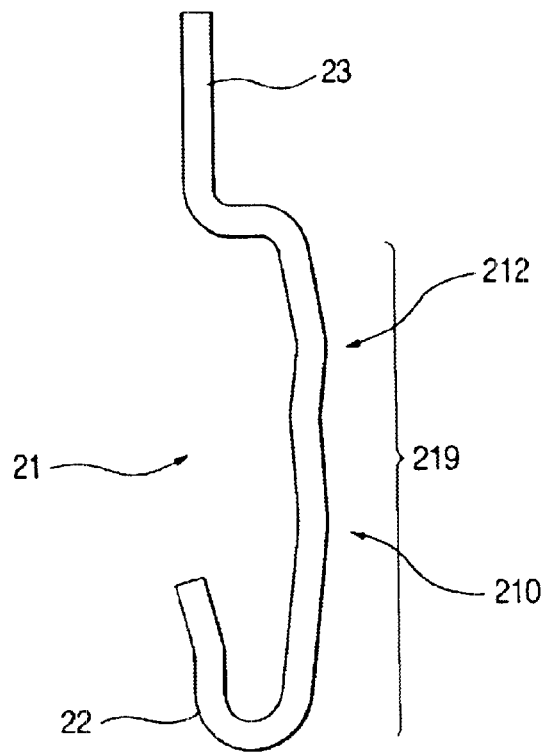
FIG. 2(b) shows a modification of the one shown in FIG. 2(a)
Figure 3:
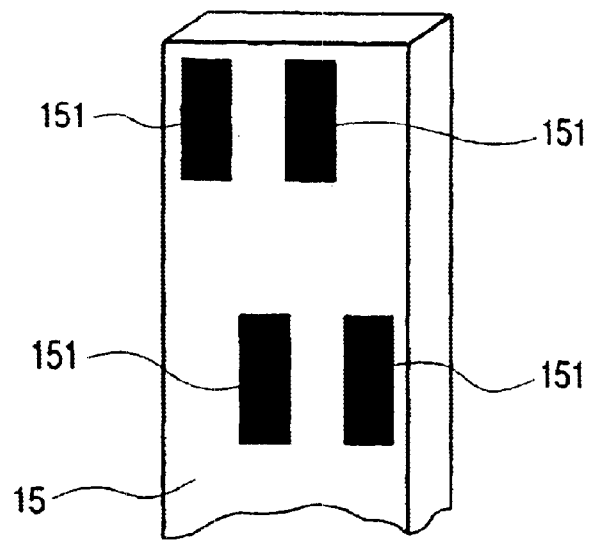
FIG. 3 is a partially perspective view which shows a sensor element on which electrode terminals are formed.

Each of the terminal pins 23 may have formed on the body portion 219, as shown in FIG. 2(b), two elastic contacts 212 and 210 either of which makes contact with one of the electrode terminals 151 located on the upper or lower side in FIG. 3. This allows the terminal pins 23 of the same type to be used for connections with the eight electrode terminals 151.

The elastic contact 210 or 212 of each of the terminal pins 23 need not always be formed to be deformable in a direction perpendicular to the longitudinal direction of the sensor element 15 (i.e., the opposed major surfaces of the sensor element 15), but may be deformable in any direction as long as the elastic pressure is produced which has a component acting in a lateral direction of the sensor element 15.

Figure 8:
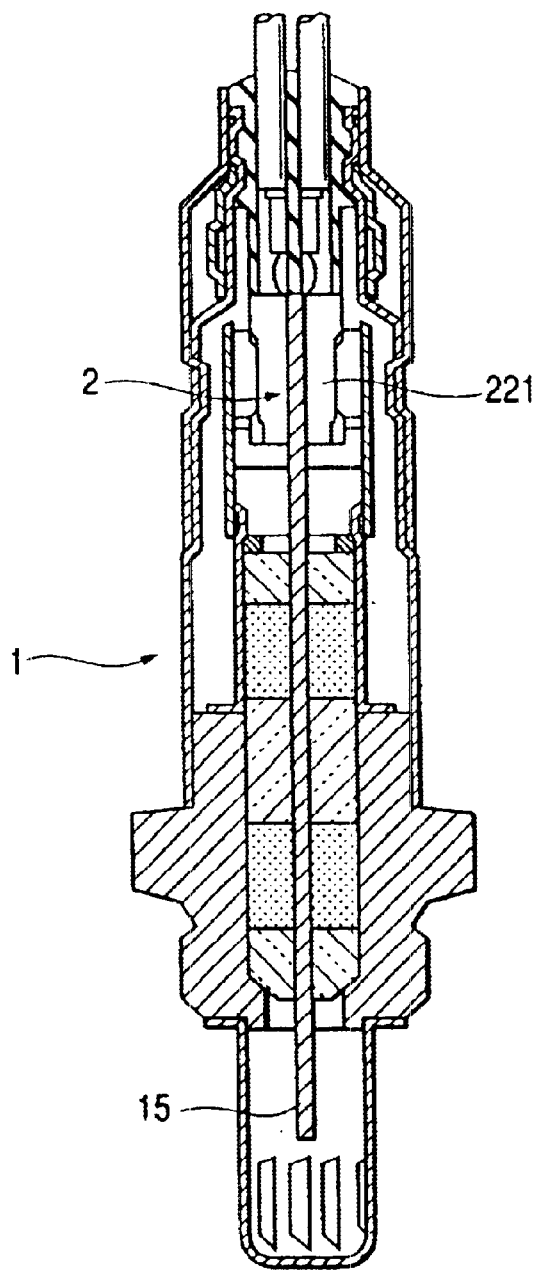
FIG. 8 is a longitudinal sectional view of a gas sensor according to the second embodiment of the invention.

FIG. 8 shows a gas sensor 1 according to the second embodiment of the invention.

Figure 9:
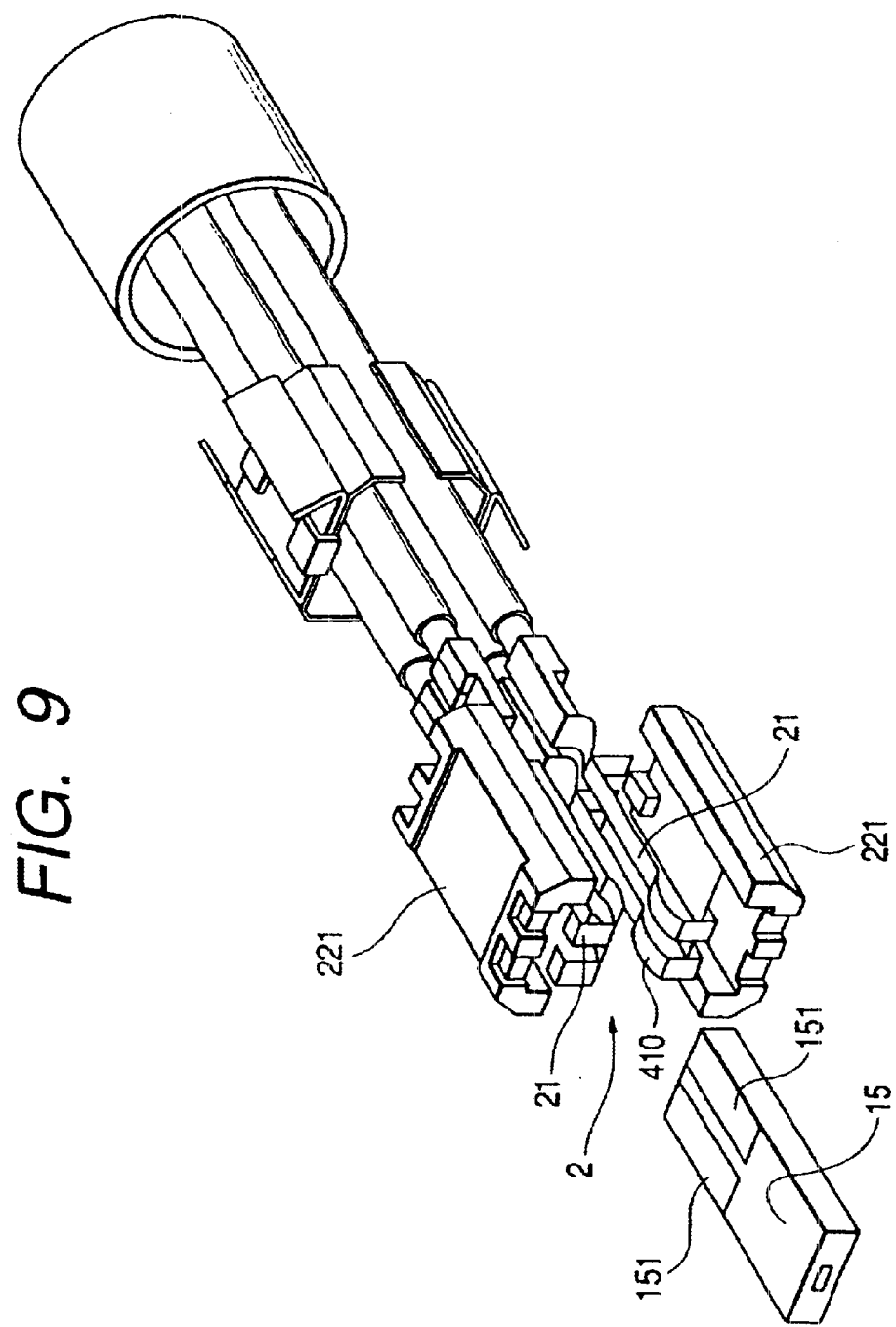
FIG. 9 is a perspective view which shows an internal structure of the gas senor of FIG. 8.

The gas sensor 1 of this embodiment, as shown in FIG. 9, has disposed therein the connector 2 which is, unlike the first embodiment, not retained by the retaining spring plate 223. The connector 2 consists of two insulating spacers 221 and four terminal strips 21 two of which are mounted on one of the insulating spacers 221. Each of the terminal strips 21 has, like the first embodiment, an elastically deformable contact 410. In the illustrated case, the sensor element 15 has two electrode terminals 151 formed on each major surface thereof which are placed within the connector 2 in electric connection to the terminal strips 21 mounted on one of the spacers 221, however, this embodiment may also be used with the sensor element 15 having three or more, preferably four or more electrode terminals 151 formed on each major surface. In this case, as many terminal strips 21 as the electrode terminals 151 formed on one of the major surfaces of the sensor element 15 are arrayed on each of the insulating spacers 221.

Figure 10:
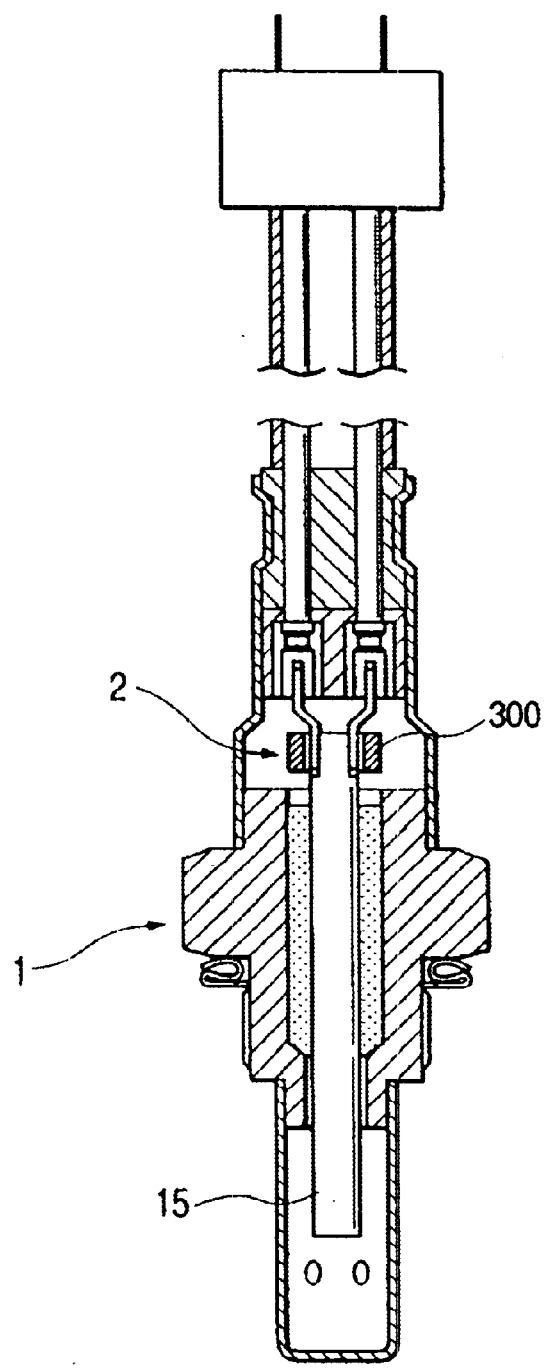
FIG. 10 is a longitudinal sectional view of a gas sensor according to the third embodiment of the invention.

FIG. 10 shows a gas sensor 1 according to the third embodiment of the invention.

Figure 11:
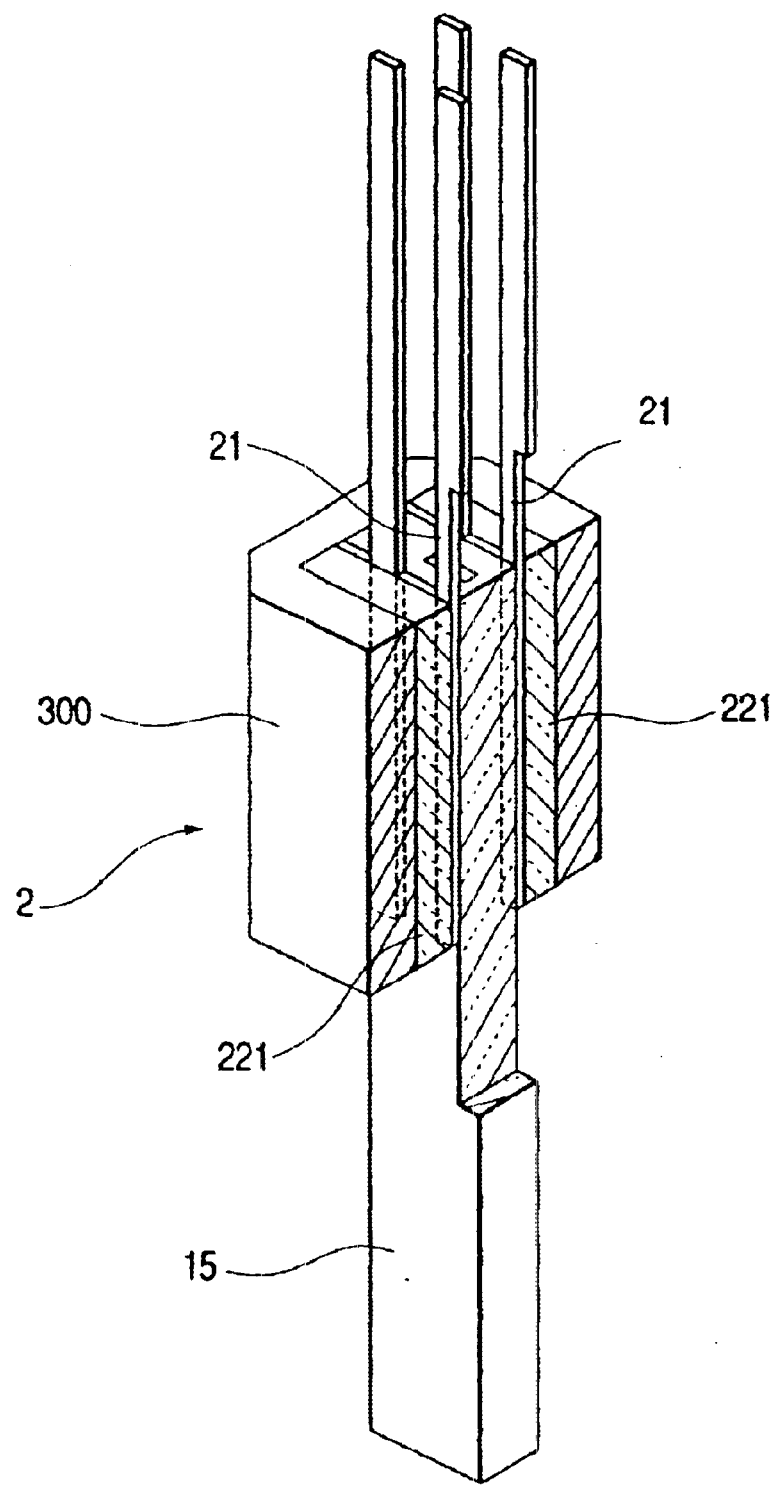
FIG. 11 is a perspective view which shows a connector disposed in the gas sensor of FIG. 10.

The connector 2 includes, as clearly shown in FIG. 11, four terminal strips 21, two insulating spacers 221, and an elastic holder 300. The elastic holder 300 is made of a C-shaped metallic member and presses two of the terminal strips 21 against each of major surfaces of the sensor element 15 elastically through the insulating spacer 221 to make firm electric connections of the terminal strips 21 with the electrode terminals 151 (not shown) of the sensor element 15. This embodiment may also be used with the sensor element 15 having three or more, preferably four or more electrode terminals 151 formed on each major surface thereof. In this case, as many terminal strips 21 as the electrode terminals 151 formed on one of the major surfaces of the sensor element 15 are retained by the holder 300 through one of the insulating spacers 221.

Figure 12:
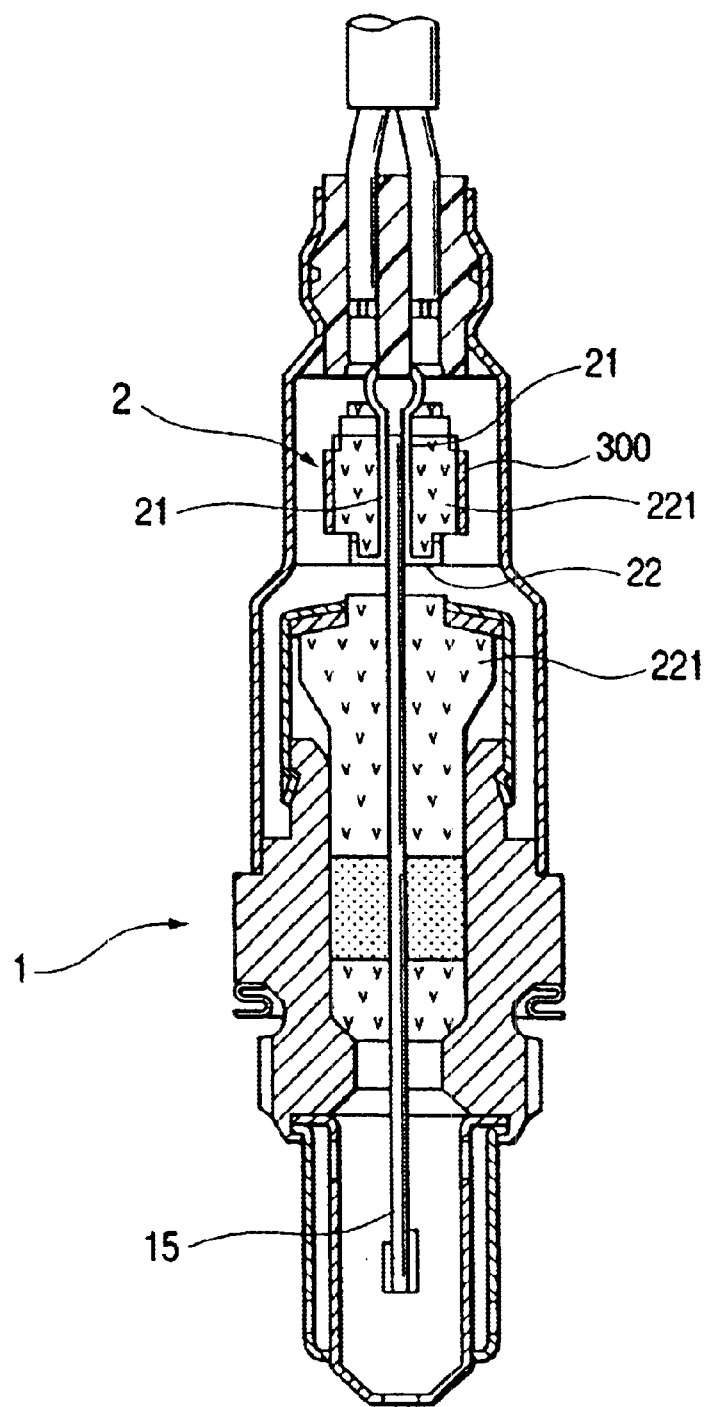
FIG. 12 is a longitudinal sectional view of a gas sensor according to the fourth embodiment of the invention.

FIG. 12 shows a gas sensor 1 according to the third embodiment of the invention which is a combination of the first and second embodiments as described above.

Specifically, the connector 2 of this embodiment has the elastic holder 300 and the insulating spacers 221 which are identical in structure with those shown in FIG. 11, however, the terminal pins 21 identical with those shown in FIG. 2(a) or 2(b) are used. Each of the terminal pins 21, as can be seen from the drawing, is fitted at the hook 22 on an end of one of the insulating spacers 221.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:

a hollow cylindrical housing;

a sensor element made of a laminated plate which includes a sensing portion and a base portion opposite the sensing portion and which has an array of electrode terminals formed on each of opposed surfaces of the base portion, said sensor element being retained at a sensing portion thereof by an insulation porcelain within said housing;

a cover covering the base portion of the sensor element;

a connector disposed within said cover, said connector having two terminal arrays each made up of four terminals making electric connections to the electrode terminals of said sensor element, wherein each array is connected electrically to one of the arrays of electrode terminals of said sensor element, each of the terminals including a contact which is elastically deformable at least in a direction substantially perpendicular to the opposed surfaces of said sensor element to establish a firm electric connection to one of the electrode terminals of said sensor element, wherein said connector includes insulating members; and a retaining spring member disposed within said cover to elastically retain each of the arrays of terminals of said connector through one of the insulating members so as to urge the terminals of said connector into constant contact with the electrode terminals of said sensor element.

2. A gas sensor as set forth in claim 1, wherein said insulating members are made of one of a ceramic material and a resin material.

3. A gas sensor as set forth in claim 1, wherein an elastic pressure produced by said retaining spring member to urge the terminals of said connector into constant contact with the electrode terminals of said sensor element is set greater than or equal to a total of elastic pressures produced by elastic deformation of the contacts of the terminals of said connector in the direction perpendicular to the opposed surfaces of said sensor element.

4. A gas sensor as set forth in claim 1, wherein an elastic pressure produced by elastic deformation of said contacts of the terminals of said connector is so set as to absorb a gap between each of said contacts and a corresponding one of the electrode terminals of said sensor element.

5. A gas sensor as set forth in claim 1, wherein each of the insulating members has an inner wall opposed to one of the surfaces of said sensor element, an end wall facing a tip of the sensing portion of said sensor element, and an outer wall opposite the inner wall, and wherein each of the terminals of said connector is curved in the shape of C so as to surround the inner wall, the end wall, and the outer wall of one of the insulating members.

6. A gas sensor as set forth in claim 1, wherein each of the terminals of said connector is made of one of a round conductive line and a rectangular conductive line.

7. A gas sensor as set forth in claim 5, wherein each of the terminals of said connector has a hook fitted on an end of one of the insulating members so that half of the terminals are arrayed on a surface of one of the insulating members.

8. A gas sensor as set forth in claim 1, further comprising a hollow insulation porcelain disposed within said cover, and wherein said retaining spring member includes a holding portion and a retaining portion, the holding portion holding the terminals of said connector through the insulating members, the retaining portion being in elastic engagement with an inner wall of said second hollow insulation porcelain so as to urge the terminals of said connector into constant contact with the electrode terminals of said sensor element.

9. A gas sensor as set forth in claim 1, wherein said retaining spring member is disposed on an outer wall of the insulating members, said retaining spring member being elastically deformable in a direction in which the insulating members are urged to ensure the constant contact of terminals of said connector with the electrode terminals of said sensor element.

10. A gas sensor as set forth in claim 1, wherein said retaining spring member includes a first spring element working to hold the insulating members together and a second spring element working to produce an elastic pressure to ensure the constant contact of the terminals of said connector with the electrode terminals of said sensor element.

* * * * *